(12) United States Patent  
Lee

(10) Patent No.: US 7,105,813 B2
(45) Date of Patent: Sep. 12, 2006

(54) METHOD AND APPARATUS FOR ANALYZING THE COMPOSITION OF AN OBJECT

(75) Inventor: Jun-Soo Lee, Yongin-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 38 days.

(21) Appl. No.: 10/924,852

(22) Filed: Aug. 25, 2004

(65) Prior Publication Data

US 2005/0056777 A1 Mar. 17, 2005

(30) Foreign Application Priority Data

Sep. 15, 2003 (KR) .................... 10-2003-0063793

(51) Int. Cl.
*H01J 37/20* (2006.01)
(52) U.S. Cl. ............... 250/309; 250/281; 250/282; 250/306; 250/307; 250/492.2; 73/864.91
(58) Field of Classification Search ............. 250/309, 250/306, 307, 281, 282, 492.2; 73/864.91
See application file for complete search history.

(56) References Cited

U.S. PATENT DOCUMENTS 5,342,448 A * 8/1994 Hamamura et al. ..... 118/723 FI
6,820,508 B1 * 11/2004 Lee ........................ 73/864.91

FOREIGN PATENT DOCUMENTS

| JP | 57-030942 | 2/1982 |
| JP | 8-254488 | 10/1996 |
| JP | 2999-123773 | 4/2000 |
| KR | 1020030023166 A | 3/2003 |

* cited by examiner

*Primary Examiner*—Nikita Wells
(74) *Attorney, Agent, or Firm*—Volentine Francos & Whitt PLLC

(57) ABSTRACT

An ion analyzing apparatus for analyzing the composition of an object includes a chamber maintained under a vacuum, a support for supporting a plurality of objects disposed in the chamber, and a drive unit that selects one of the supported objects and rotates the selected object. An ion generator irradiates the rotating object with primary ions. A detector detects secondary ions emitted from the rotating object. An analyzer analyzes the secondary ions. A transfer device is connected to the supporter. The transfer device rotates the support or moves the support linearly in a horizontal direction to place an object at a predetermined position at which the object is selected and rotated by the drive unit.

22 Claims, 7 Drawing Sheets

METHOD AND APPARATUS FOR ANALYZING THE COMPOSITION OF AN OBJECT

BACKGROUND OF THE INVENTION

1. Field of the Invention

The present invention relates to the analyzing of an object to determine a composition of a layer of the object. More particularly, the present invention relates to a method of and apparatus for analyzing ions in a layer of an object using secondary ion mass spectrometry.

2. Description of the Related Art

Semiconductor devices having a high degree of integration and which operate reliably at a high speed have been developed to process massive amounts of data in a short amount of time. In general, such highly integrated semiconductor devices are fabricated by performing various processes on a semiconductor substrate. These processes include, for example, a process of forming a layer on the substrate, an ion implantation process, an etching process, and a process for forming a wiring pattern on the substrate. Ultimately, though, the semiconductor devices must be analyzed to detect for processing failures or the like.

One apparatus for analyzing an object, such as a semiconductor device, is a secondary ion mass spectrometer (SIMS). The SIMS irradiates first ions having a kinetic energy of about 0.5 keV to about 20 keV onto a surface of the object such as a semiconductor device to break the bonds between the atoms or molecules of a material that makes up the surface of the object. The breaking of the bonds by the first ions is referred to as a sputtering. Thus, it can be said that the material is broken down into elementary particles by an elementary or a molecular unit by the sputtering. These particles are partially ionized to create secondary ions. The secondary ions are then supplied to an ion analyzer. The ion analyzer classifies the secondary ions according to their energy or mass to determine the composition of the material.

A SIMS may be used to perform a mass spectrum inspection, a depth profiling inspection, an ion imaging inspection and a quantification inspection of an object. The mass spectrum inspection determines the numbers of different types of secondary ions according to the ratio of the mass of each secondary ion to the electric charge of the secondary ion, to thereby provide a representation of the kinds of atoms in and composition of the surface of the object. The numbers of the secondary ions are counted at a rate of above about 1 count/sec. to about $10^9$ counts/sec. Accordingly, the numbers of the secondary ions are provided on a logarithmic scale. Also, the masses of the secondary ions detected using the mass spectrum inspection method are about 1 atomic mass unit (amu) to about 300 amu. Accordingly, the mass spectrum inspection method can also be used to determine the molecules, particle clusters and isotopes making up the material of the object.

The depth profiling inspection discriminates particular ions from among the secondary ions. Intensity levels of the selected ions are measured over time to determine a distribution of the selected ions over the depth of the object.

The ion imaging inspection correlates the secondary ions to the positions at which they were generated, and measures the intensities of the secondary ions. For example, the ion imaging inspection scans the object with ions having a diameter of about 1 µm, and measure intensities of the secondary ions produced during the scan. The ion imaging inspection thus determines the distribution of the secondary ions across the surface of the object.

The quantification inspection simultaneously analyzes the object and a standard object under same conditions. The standard object is fabricated by an ion implantation process so that it has ions in a concentration and at a depth which are known. A comparison between the standard object and the object being analyzed is used to obtain the concentration and depth of particles making up the object under analysis.

When used to carry out the inspection methods described above, a SIMS has a good deal of sensitivity and a wide detection range. That is, a SIMS can be used to detect infinitesimally small particles in amounts of parts per million to parts per billion. Additionally, a SIMS can detect every element in the Periodic Table, and even the isotopes thereof.

In addition, a SIMS has the ability to perform a depth profiling of about 4 nm and a line scanning of about 200 nm. Accordingly, a SIMS is useful for detecting impurities in a semiconductor device. However, certain phenomena such as a surface effect, an interface effect, an electric charge effect, and a mass interference effect, can limit the effectiveness of the SIMS when applied to detecting impurities in a semiconductor device.

The surface effect is a phenomenon in which the profile of the surface due to first ions are implanted into the surface of the object and into contaminants on the surface of the object. The profile of the surface displayed as a result differs from that actually exhibited by the surface. The interface effect is a phenomenon in which the locations of an interface in the object are inaccurately displayed due to a number of factors such as the surface roughness of the object, variations in the first ions, and contaminants.

The electric charge effect is a phenomenon in which charges accumulate on the surface of the object due to a collision of the first ions, and the generation of the secondary ions. The mass interference effect is a phenomenon in which a single atomic ion interferes with a molecular ion and a multiple charged ion.

It has thus been proposed to rotate the object during its analysis as a way to lessen the effects of the above-described phenomena on the inspection method carried out by a SIMS. When a rotating object is irradiated with the first ions, the sputtering rates of the atoms in the object vary so that minute impurities contained in the object can be detected. Accordingly, a composition of the object can be precisely analyzed.

FIG. 1 is a graph showing an analysis of a semiconductor device using a conventional analyzing method. FIG. 2 is a graph showing an analysis of a semiconductor device using a conventional rotation analyzing method in which the semiconductor device is rotated. The semiconductor device includes a silicon layer, a titanium layer formed on the silicon layer, and a gold layer formed on the titanium layer.

A surface of the semiconductor device was irradiated with primary ions. The primary ions etched the surface of the semiconductor device. Thus, the particles detected over time corresponded to the layers of the semiconductor device in a depth-wise direction of the semiconductor device, respectively. Particles of gold, titanium and silicon layer were detected over time, as shown in FIGS. 1 and 2.

However, the interfaces of the layers were detected imprecisely in the results of the method shown in FIG. 1. In particular, the gold layer was detected in a range A and the titanium layer was detected in a range B that overlapped range A to a great extent. Thus, the gold layer infiltrated the titanium layer. Also, the results showed that the titanium layer infiltrated the silicon layer.

On the contrary, in the method shown in FIG. 2, after about 900 seconds, that is a range A', the gold layer was not detected. After about 1,100 seconds, that is in a range B', the titanium layer was not detected. Thus, as these results show, the method of analyzing a rotating object can determine the composition of a semiconductor device with better accuracy than a method of analyzing the semiconductor device while it is stationary.

However, analyzing a plurality of objects using a conventional SIMS is difficult. When a single object having a diameter of about 80 mm is disposed on a stage in an ion chamber of the SIMS, it is relatively easy to rotate the object by rotating the stage about its center. However, it becomes more difficult to control the rotation of the stage the larger the stage becomes. Therefore, when a large number of objects are disposed on a stage in the chamber of the SIMS, rotating the objects is problematic because the stage must be large enough to accommodate all of the objects. Furthermore, the object under analysis on the rotating stage might not be accurately irradiated with the primary ions. As a result, although the object is analyzed while it is rotated, the accuracy of the analysis can be expected to be poor.

Furthermore, various conditions are created in the ion chamber to facilitate the analysis of an object. Therefore, when objects are placed one-by-one in the ion chamber and analyzed, the atmosphere within the ion analysis chamber must be checked and often adjusted each time. Accordingly, a large amount of time is required for analyzing the objects which adds which to the overall costs associated with the analyzing process.

SUMMARY OF THE INVENTION

An object of the present invention is to provide a method and apparatus that are capable of analyzing the compositions of a plurality of objects rapidly and accurately.

Another object of the present invention is to provide a compact apparatus that is capable of accurately analyzing the compositions of a plurality of objects.

According to one aspect of the present invention, a method of analyzing an object begins by disposing a plurality of objects in a chamber maintained under a predetermined pressure. One of the objects is selected and moved to a fixed analysis position in the chamber. The selected object is then rotated at the analysis position. Then, the rotating object is irradiated with primary ions produced by an ion generator. Secondary ions emitted from the rotating object as the result of the object being irradiated are collected and analyzed. The process is then repeated for the other objects in sequence.

According to another aspect of the present invention, an apparatus for analyzing an object includes a chamber that is isolated from the exterior so that it can be maintained under a predetermined pressure, and a support configured to support a plurality of objects is disposed in the chamber. A drive unit selects one the objects and then rotates the selected object. An ion generator irradiates the rotating object with primary ions. A detector detects secondary ions emitted from the rotating object, and an analyzer analyzes the collected secondary ions.

In addition, a transfer device is connected to the support. The transfer device rotates or moves the support linearly in a horizontal plane to move one of the objects to a predetermined position in preparation for the object being irradiated with the primary ions produced by the ion generator.

According to the present invention, the compositions of the objects are precisely analyzed by rotating the objects as they are irradiated. Each of objects disposed in the chamber is rotated individually at a set location within the chamber while it is analyzed. Thus, the rotation of objects does not require a great deal of space in the chamber. Therefore, defects or impurities in the objects are accurately detected so that errors in the process or processes used to manufacture the objects may be reduced.

BRIEF DESCRIPTION OF THE DRAWINGS

The above and other features and advantages of the invention will become readily apparent by referring to the following detailed description of the preferred embodiments thereof made in conjunction with the accompanying drawings wherein.

DETAILED DESCRIPTION OF THE PREFERRED EMBODIMENTS

Embodiments of a method of and an apparatus for analyzing an object in accordance with the present invention will now be described detail.

Figure 1:
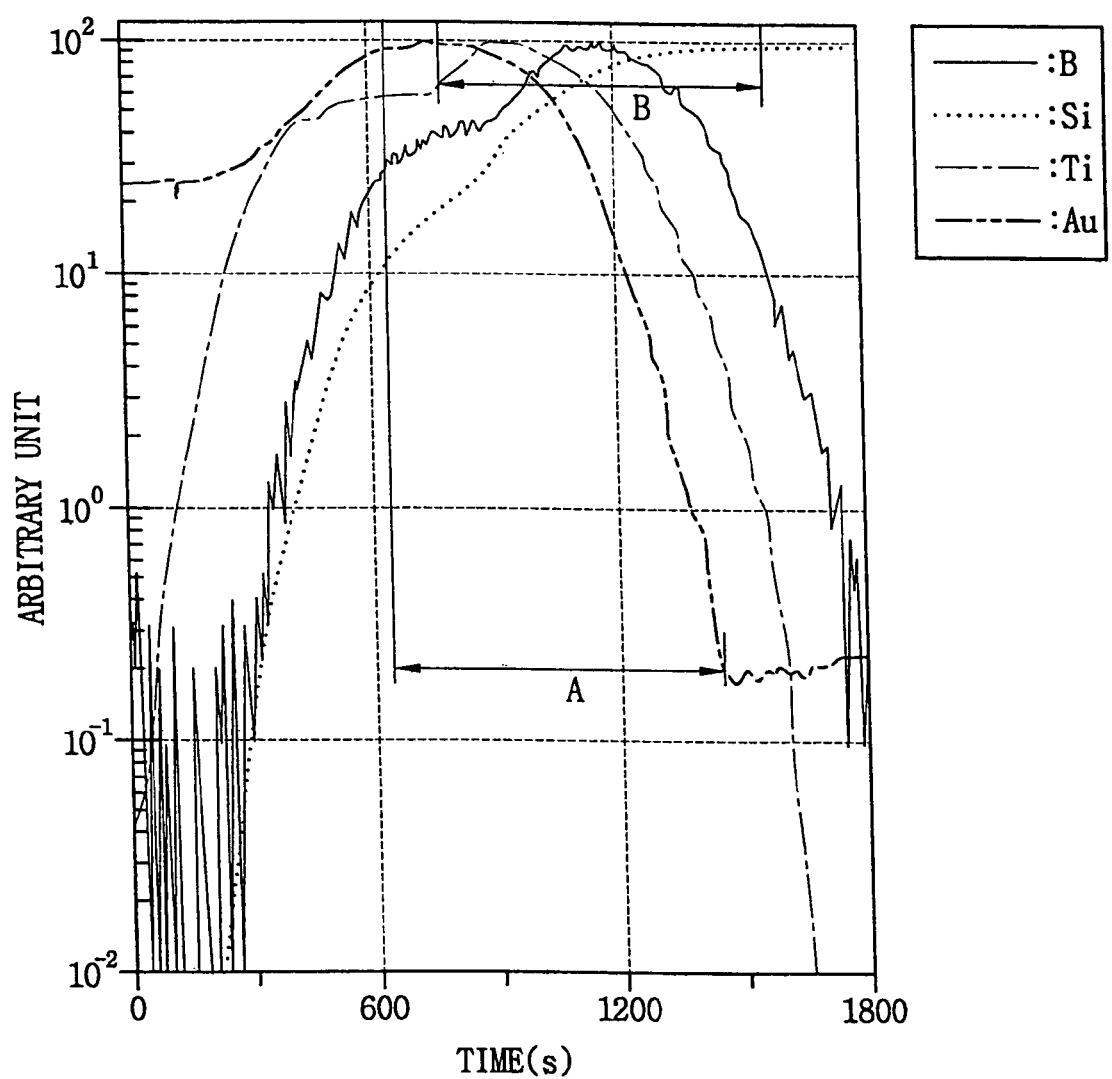
FIG. 1 is a graph showing an analysis of a semiconductor device in accordance with a conventional method.
Figure 2:
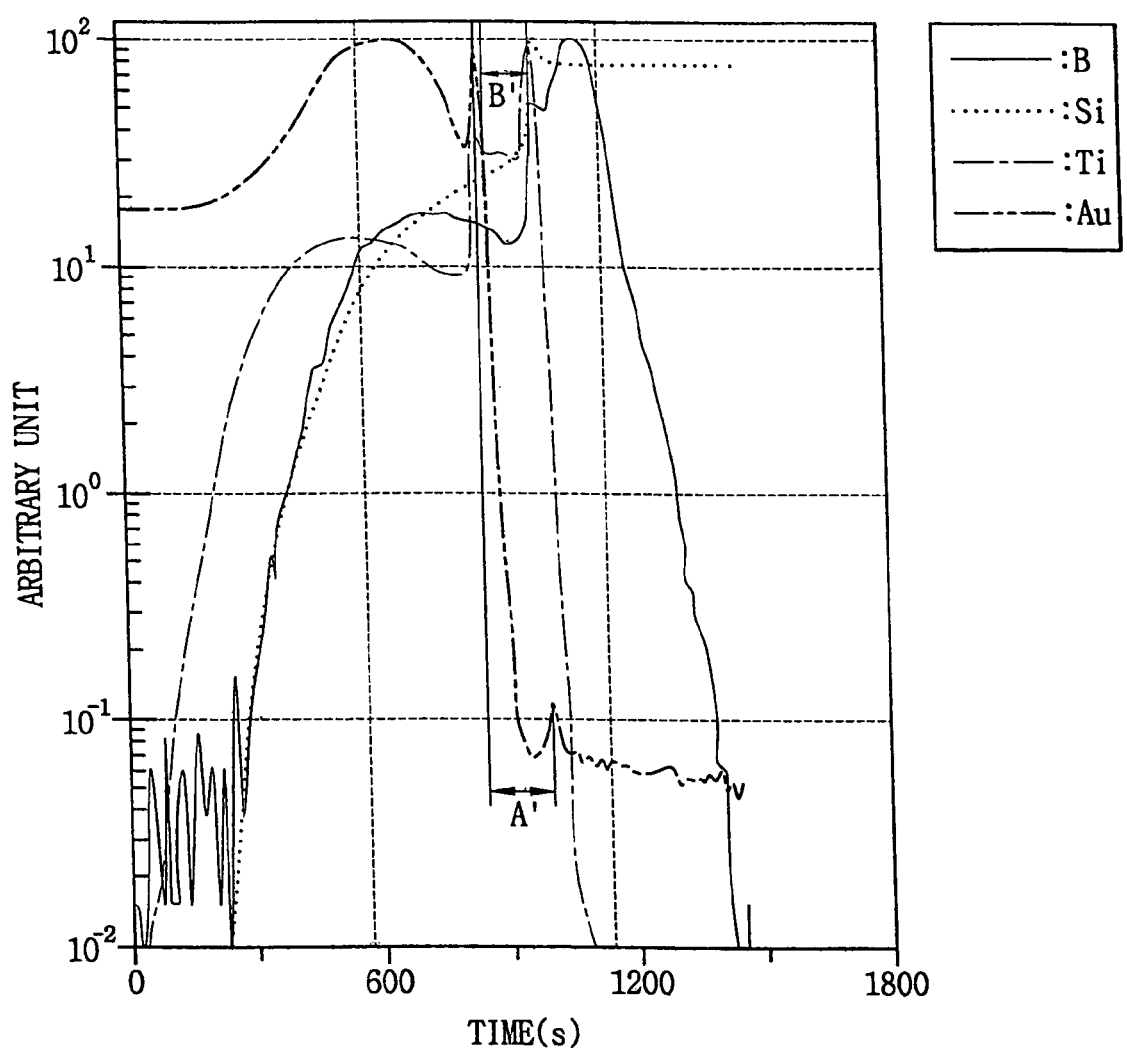
FIG. 2 is a graph showing an analysis of a semiconductor device in accordance with a conventional method that includes rotating the device.
Figure 3:
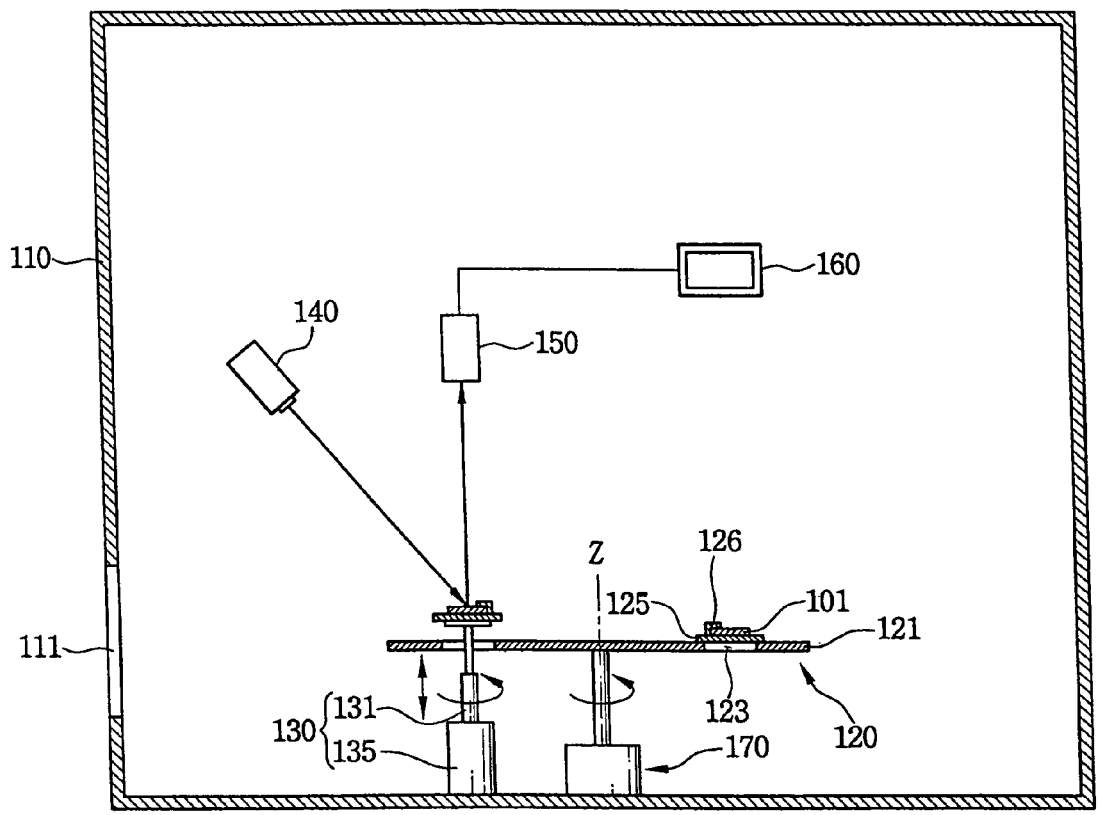
FIG. 3 is a sectional view of a first embodiment of an apparatus for analyzing an object in accordance with the present invention.
Figure 4:
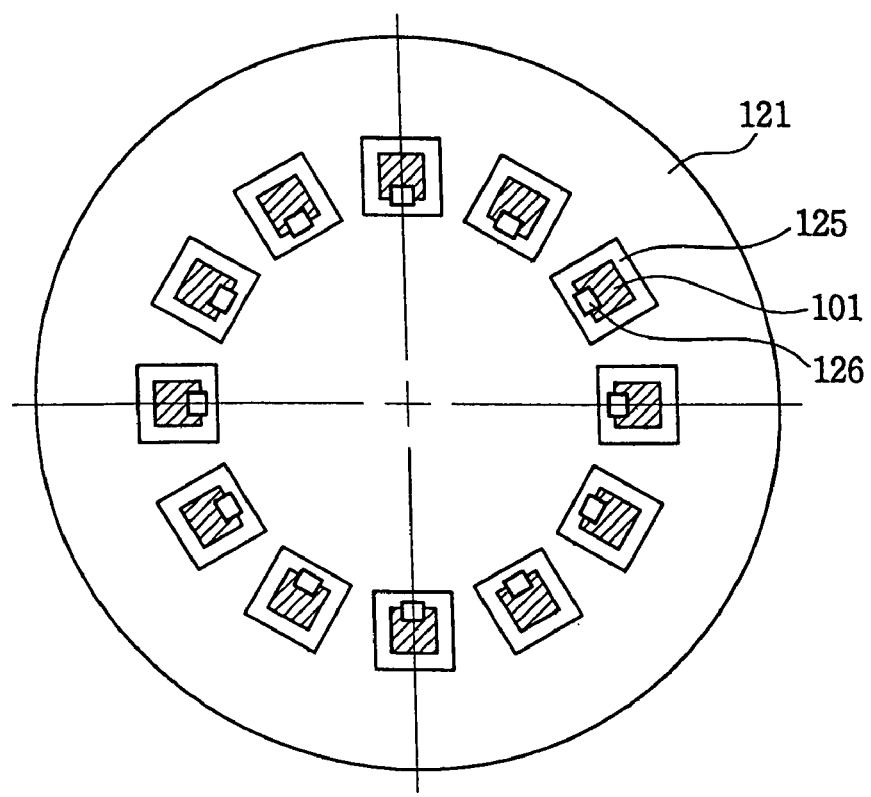
FIG. 4 is an enlarged plan view of a support of the apparatus shown in FIG. 3.

Referring first to FIGS. 3 and 4, an apparatus for analyzing the composition of a layer of an object includes a chamber 110 in which vacuum is produced. A support 120 on which a plurality of objects 101 rest is disposed in the chamber 110. A drive unit 130 is disposed under the support 120. The drive unit 130 operates to select one of the objects 101 and then rotates the selected object 101. An ion generator 140 irradiates the rotating object 101 with primary ions. A detector 150 collects secondary ions emitted from the rotating object 101. An analyzer 160 analyzes the secondary ions collected in the detector 150.

The inside of the chamber 110 is isolated from the environment outside the chamber. A door 111 is provided at one side of the chamber 110. The objects 101 are loaded into the chamber 110 through the door 111. A vacuum pump (not shown) is connected to the chamber 110 to produce a vacuum in the chamber 110. The chamber 110 is preferably maintained under a pressure of about $1.3 \times 10^{-11}$ Torr to about $1.3 \times 10^{-7}$ Torr.

The support 120 extends horizontally in the chamber 110. The objects 101 are disposed on and supported by the support 120. The support 120 includes a circular plate 121 having a plurality of holes 123 arrayed along the circumference of the plate 121. The objects 101 are disposed over the holes 123 with the central axes of the objects coinciding with the centers of the holes 123, respectively. Additionally, a holder 125 may be disposed over each of the holes 123. In this case, each of the objects 101 is disposed on a respective holder 125.

The holders 125 facilitate the rotating of the objects 101. Each holder 125 has a diameter greater than that of the hole 123 over which it is disposed so that it covers or otherwise closes the hole 123. The holders 125 may also be detachably mounted to the plate 121. Each holder 125 may also have a projection 126 into which the object 101 is inserted to fix the object 101 on the holder 125. Alternatively, the holder 125 may have a vacuum chuck, an electromagnet or a fixing tool, instead of the projection 126, to fix the object 101 to the holder 125.

A transfer device 170 is connected to the support 120 to rotate the support 120 about a vertical axis Z. To this end, the transfer device 170 includes a rotary drive mechanism, such as a rotary motor, connected to the center of the bottom of the plate 121. The distance between the drive unit 130 and the axis Z is substantially identical to that between the center of the plate 121 and the array of holes 123. Accordingly, each of the holes 123 may be positioned over the drive unit 130.

The drive unit 130 includes an arm 131 for supporting a selected object 101, and a driving mechanism 135 for moving the arm vertically and rotating the arm 131. The arm 131 may be extendable in a vertical direction. For example, the arm 131 may be telescopic. Alternatively, the arm 131 may comprise a plurality of links that can be articulated by the driving mechanism, or a single link structure that can be moved upwardly in its entirety by the driving mechanism 135. Also, although FIG. 3 shows a single driving mechanism 135 as being provided for extending and rotating the arm 131, two independent and discrete driving mechanisms may be provided instead, i.e., a first driving mechanism operative to move the arm 131 vertically and a second driving mechanism operative to rotate the arm 131 about the vertical axis. The driving mechanism(s) may comprise gears, belts, pulleys, chains, motors, bellows, hydraulic units, pneumatic units, etc.

During operation, the arm 131 is moved vertically through a hole 123 by the driving mechanism 135 and into contact with the bottom surface of a selected object 101 or holder 125 to which the object 101 is mounted. The object 101 is thus supported by the upwardly moving arm 131 and raised from the plate 121 by the arm 131. The object 101 is also rotated by the arm 131.

The ion generator 140 for generating primary ions is disposed over the support 120. The ion generator 140 is inclined relative to the plate 121, i.e., to the horizontal, by an angle of about 45° to about 90°. Thus, the ion generator 140 irradiates the rotating object 101 with primary ions at an angle of about 45° to about 90°.

The primary ions may be created from gas that includes oxygen ($O_2$), cesium (Cs), gallium (Ga), argon (Ar), etc. These can be used alone or in a mixture thereof. Thus, the primary ions may be $O_2^+$, $O^+$, $Cs^+$, $Ga^+$, $Ar^+$ ions or mixtures thereof. The primary ions preferably have an energy level of about 0.5 KeV to about 20 KeV. Also, the primary ions may be emitted onto the selected object 101 through lenses.

The primary ions break the bonds of the materials comprising the object 101 to generate elemental, neutral or molecular particles. That is, the object 101 is sputtered by the primary ions. Some of the elemental, neutral or molecular particles are ionized to form secondary ions.

Currently, highly integrated semiconductor devices have very thin junctions or layers on the order of below about tens of angstroms (Å). The primary ions must have an energy range in which a knock-on effect does not occur if the layers of a such highly integrated semiconductor device are to be analyzed in its depth-wise direction. The primary ions used for analyzing a typical thin layer have an energy level of about 10 KeV to about 12.5 KeV. The primary ions used for analyzing an interface between the thin layers have an energy level of about 500 KeV to about 5 KeV. However, the primary ions will, of course, be given an energy level based on the object 101 to be analyzed.

In any case, the secondary ions discharged from the selected object 101 are transmitted to the analyzer 160 through the detector 150. The detector 150 is disposed substantially perpendicular to the object 101. However, the detector 150 may be positioned otherwise, in accordance with kinds of secondary ions, to readily detect the desired secondary ions. The detector 150 may comprise an electron multiplier, a faraday cup, or an ion sensitive image amplifier.

The analyzer 160 receives the secondary ions collected in the detector 150, and accelerates the secondary ions using an electric field to analyze the energy and mass of the accelerated secondary ions. To this end, the analyzer 160 may include an energy analysis unit and a mass analysis unit. More specifically, the analyzer may comprise a magnetic mass analyzer, a quadruple mass analyzer or a time of flight mass analyzer. The analysis of the secondary ions performed by the analyzer 160 determines the composition of the selected object 101.

When the analysis of the selected object 101 is completed, the arm 131 is lowered to place the analyzed object 101 back on the support 120. The support 120 is then rotated to select another object 101, i.e., to place another object above the drive unit 130. The above-described process is then repeated for the newly selected object 101.

According to the present embodiment, a plurality of objects 101 are sequentially selected and rotated. The primary ions are emitted onto each rotating object. Therefore, each of the objects 101 is analyzed while being individually rotated. Accordingly, the apparatus of the present invention is compact and may thus be employed in a chamber of a conventional SIMS analysis apparatus. Further, the secondary ions can be analyzed with a remarkable degree of accuracy.

Figure 5:
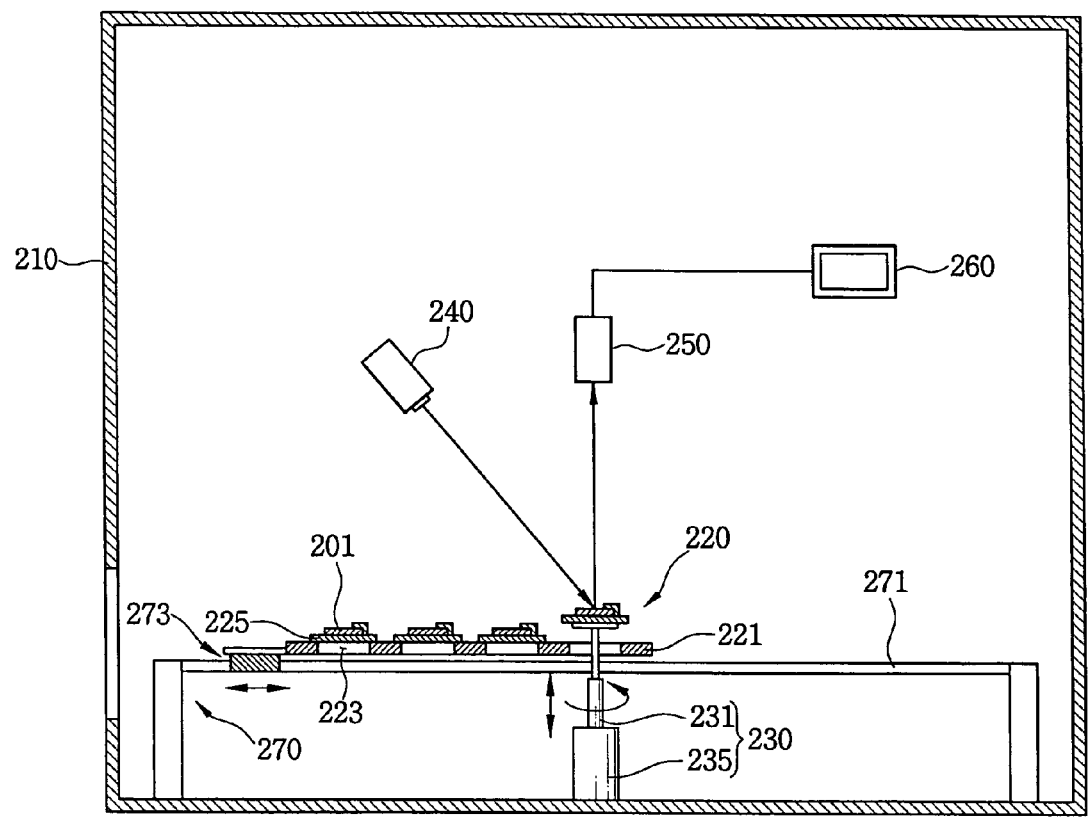
FIG. 5 is a sectional view of a second embodiment of an apparatus for analyzing an object in accordance with the present invention.
Figure 6:
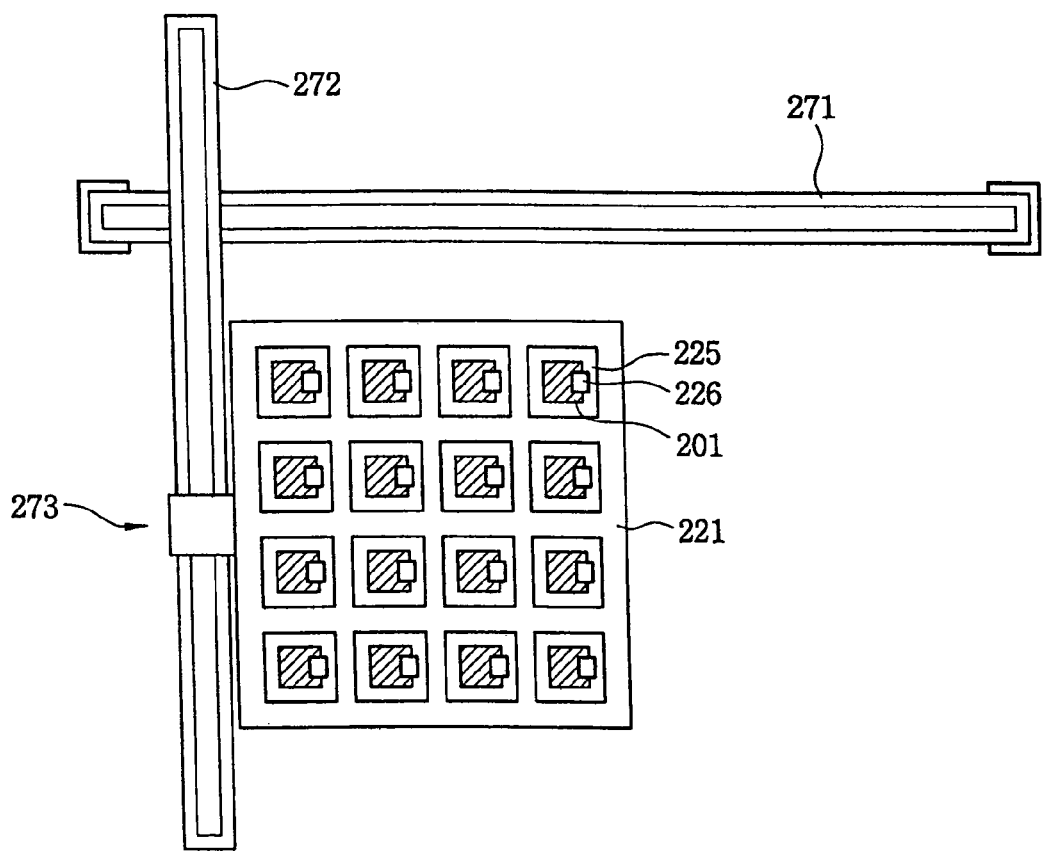
FIG. 6 is an enlarged plan view of a support of the apparatus shown in FIG. 5.

FIGS. 5 and 6 illustrate another embodiment of an apparatus for analyzing an object in accordance with the present invention. The apparatus includes a chamber 210 in which a vacuum is created. A support 220 on which a plurality of objects 201 is disposed is provided in the chamber 210. A drive unit 230 is disposed under the support 220. The drive unit 230 is operative to select one of the objects 201 and then rotate the selected object 201. An ion generator 240 irradiates the rotating object 201 with primary ions. A detector 250 collects secondary ions emitted from the rotating object 201. An analyzer 260 analyzes the secondary ions collected by the detector 250.

The chamber 210, the drive unit 230, the detector 250 and the analyzer 260 are substantially identical to those of the embodiment of FIGS. 3 and 4.

The support 220 includes a square plate 221 through which holes 223 extend. Holders of the type (125) shown in FIGS. 3 and 4 may be provided on the plate 221. A transfer device 270 moves the support 220 in a horizontal plane. The transfer device 270 may comprise a gear unit such as a rack and pinion, a hydraulic/pneumatic unit such as a hydraulic/pneumatic cylinder or a motorized unit such as a guide rail and linear motor. In the present embodiment, the transfer device 270 is a motorized unit including a guide rail and linear motor.

More specifically, the transfer device 270 includes an X-axis rail 271, a Y-axis rail 272 disposed substantially perpendicular to the X-axis rail 271, and linear motors 273 mounted on the X- and Y-axis rails 271 and 272, respectively. The X-axis rail 271 is fixed to a bottom surface of the chamber 210. The Y-axis rail 272 is movably disposed on the X-axis rail 271. The plate 221 is mounted to the Y-axis rail 272. The holes 223 in the plate 221 are arrayed in rows and columns parallel to the X- and Y-axis rails 271, 272.

The drive unit 230 includes an arm 231 for supporting a selected object 201, and a driving mechanism 235 for moving the arm vertically and rotating the arm 231. The arm 231 may be extendable in a vertical direction. For example, the arm 231 may comprise a plurality of links that can be articulated by the driving mechanism, or a single link structure that can be moved upwardly in its entirety by the driving mechanism 235. Also, although FIG. 5 shows a single driving mechanism 235 as being provided for extending and rotating the arm 231, two independent and discrete driving mechanisms may be provided instead, i.e., a first driving mechanism operative to move the arm 231 vertically and a second driving mechanism operative to rotate the arm 231 about the vertical axis Z. The driving mechanism(s) may comprise gears, belts, pulleys, chains, motors, bellows, hydraulic units, pneumatic units, etc.

During operation, the arm 231 is moved vertically through a hole 223 by the driving mechanism 235 and into contact with the bottom surface of a selected object 201 or holder 225 to which the object 201 is mounted. The object 201 is thus supported by the upwardly moving arm 231 and raised from the plate 221 by the arm 231. The object 201 is also rotated by the arm 231.

The ion generator 240 for generating primary ions is disposed over the support 220. The ion generator 240 is inclined relative to the plate 121, i.e., to the horizontal, by an angle of about 45° to about 90°. Thus, the ion generator 240 irradiates the rotating object 201 with primary ions at an angle of about 45° to about 90°.

When the analysis of the selected object 201 is completed, the arm 231 is lowered to place the analyzed object 201 back on the support 220. The support 220 is then moved along the X-axis rail 271 or the Y-axis rail 272 to place another object 201 above the drive unit 230. The arm 231 is then upwardly moved and rotated so that this newly selected object 201 is rotated on the arm 231. The newly selected object 201 is irradiated with primary ions. The secondary ions emitted from the newly selected object 201 are detected and analyzed.

In this way, the objects 201 are sequentially placed in an analysis position relative to the ion generator 240. Therefore, all of the objects 201 can be rotated and analyzed without changing the atmosphere within the chamber 210.

Figure 7:
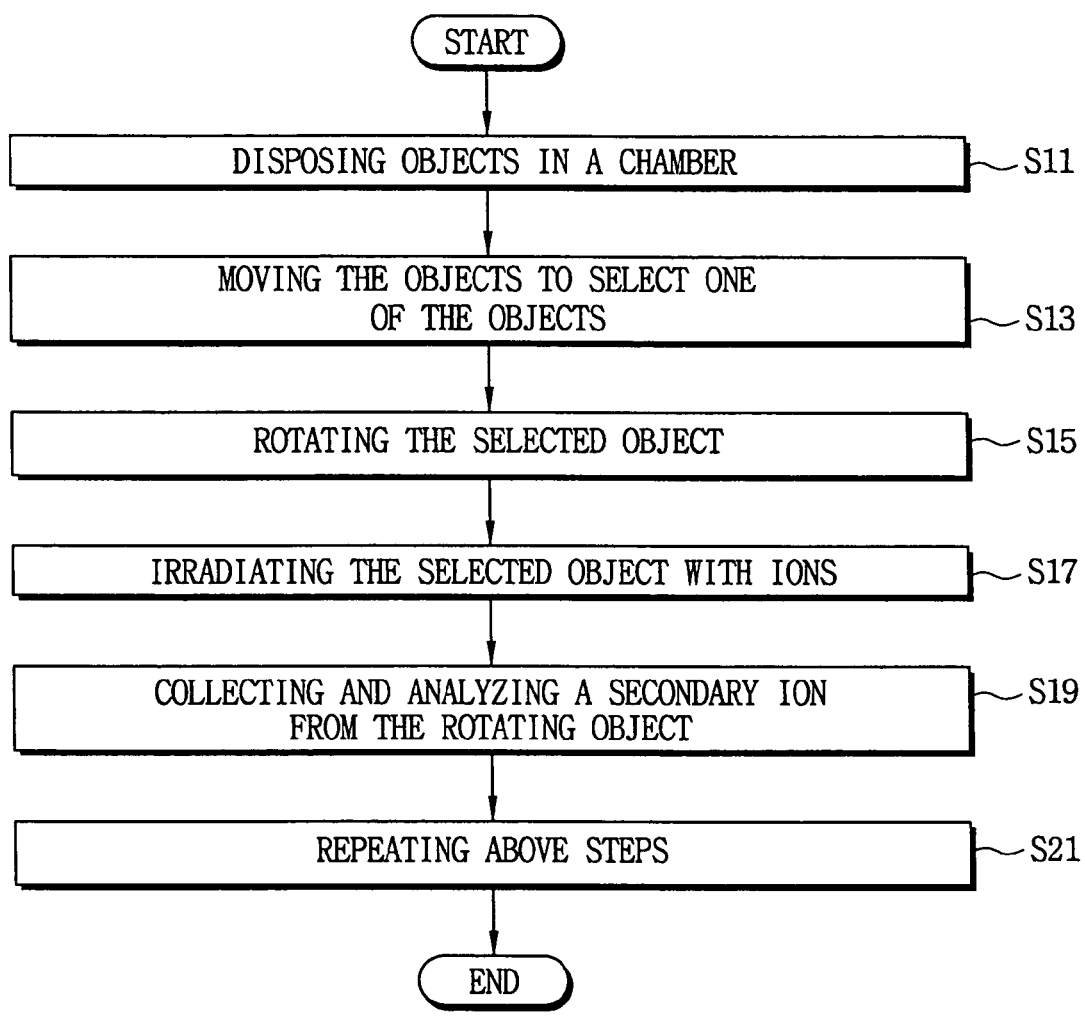
FIG. 7 is a flow chart illustrating a method of analyzing an object in accordance with the present invention.

Hereinafter, an embodiment of a method of analyzing objects in accordance with the present invention will be described with reference to FIG. 7.

First, a plurality of objects is disposed in a chamber maintained under a predetermined (vacuum) pressure (step S11). Next (step S13), all of the objects are moved at once until a selected one of the objects is placed at a predetermined position in the chamber. The selected object is placed at an analysis position with respect to an ion generator. The selected object is then rotated (step S15). Primary ions are produced by an ion generator and the rotating object is irradiated with the primary ions (step S17). Secondary ions emitted from the rotating object are collected and analyzed (step S19). Finally, (step S21), steps S11 to S19 are repeated for each of the other objects.

More specifically, in step S11, the objects are situated in the same plane in the chamber. In step S13, the objects are moved all at once within that plane until a selected one of the objects is disposed at a predetermined position in the chamber. For example, the objects are all rotated about a vertical axis. Alternatively, the objects are moved linearly along X and/or Y axes extending perpendicular to one another.

The object moved is then raised above the aforementioned plane. In step S15, the selected object is rotated around a vertical axis. Alternatively, the axis of rotation of the object may be inclined relative to the vertical. Also, the axis about which the selected object is rotated preferably coincides with the center of the object.

In step S17, the selected object is irradiated with primary ions emitted from an ion generator. The primary ions are directed onto the selected object at an angle of incidence of about 45° to about 90°. The primary ions may be created from oxygen ($O_2$), cesium (Cs), gallium (Ga), argon (Ar), etc. These gases can be used alone or in a mixture thereof. Thus, examples of the primary ions include $O_2^+$, $O^+$, $Cs^+$, $Ga^+$, and $Ar^+$ ions. The intensity of the primary ions is determined according to the type of object being analyzed. In the case of semiconductor devices, the primary ions preferably have an energy level of about 0.5 KeV to about 20 KeV.

The primary ions break the molecular bonds of the material constituting the selected object to generate elemental, neutral or molecular particles. Some of the elemental, neutral or molecular particles are ionized to form secondary ions. In step S19, the secondary ions are collected using an electron multiplier, a faraday cup, an ion sensitive image amplifier, or the like. Optionally, the secondary ions may be classified according to their energy Selected ones of the classified secondary ions may be accelerated and then collected.

The collected secondary ions are analyzed to determine the composition of the object. To this end, the secondary ions may be directed through a magnetic mass analyzer, a quadruple mass analyzer, a time of flight (TOF) mass analyzer or the like.

In step S21, the above-described steps S11 to S19 are repeated for the remainder of the objects. Once the compositions of the objects are determined, impurities in the objects are identified. Accordingly, failures in the processes used for fabricating the objects may be determined.

According to the present invention as described above, a plurality of objects to be analyzed is disposed in a single chamber maintained under a constant pressure. One of the objects is then selected, rotated, irradiated with primary ions, and analyzed. Then the process is repeated for each of the other objects. Accordingly, the rotating objects are analyzed separately and subsequently but under the same conditions. Thus, the analyses of the objects may be compared and certain relationships among the objects may be readily deduced. Furthermore, only a small amount of time, if any, is required to establish the conditions such as pressure, temperature and voltage in the chamber in preparation for the analysis of each of the objects. Thus, a plurality of objects can be precisely analyzed in a short amount of time. Still further, the apparatus is compact because a drive unit and a support stage are used to rotate each of the several objects. Accordingly, the apparatus may be embodied using a conventional ion chamber of a SIMS.

Although the present invention has been described above in connection with the preferred embodiments thereof, it is noted that modifications and variations of these preferred embodiments will become readily apparent to those of ordinary skill in the art.

For example, although the plate of the support 120, 220 was described above as being circular or square, the present invention is not so limited. Rather, the plate may also have other shapes wherein the relative locations of the holes therethrough will depend on the shape of the plate. Also, the objects do not have to be supported on a movable plate. Rather, a turntable that is rotatable about a vertical axis may be disposed in the chamber, and the objects are disposed on a stationary support adjacent the turntable. The objects are transferred onto the turntable using a robot arm.

It is therefore to be understood that various changes may be made to the preferred embodiments of the present invention within the true scope and the spirit of the invention as defined by the appended claims.

What is claimed is:

1. A method of analyzing the composition of an object, comprising:
   (a) disposing a plurality of objects all together in a chamber;
   (b) selecting one of the objects and moving the selected object to a fixed analysis position in the chamber;
   (c) rotating the selected object, independently of the other objects, at the analysis position while the other objects are maintained stationary;
   (d) irradiating the rotating object with primary ions produced by an ion generator;
   (e) collecting secondary ions emitted from the rotating object as the result of the object being irradiated;
   (f) analyzing the collected secondary ions to determine a composition of the object;
   (g) subsequently selecting another one of the objects;
   (h) moving the another one of the objects to said analysis position;
   (i) rotating the selected another one of the objects at the analysis position; and
   (j) performing (d)–(f) on said another one of the objects.

2. The method of claim 1, wherein said (a) disposing the objects in the chamber comprises situating the objects all in the same horizontal plane, and said (b) selecting and moving one of the objects to the analysis position comprises raising the selected object from said horizontal plane while the other objects remain in the horizontal plain.

3. The method of claim 1, wherein said (c) rotating the selected object comprises rotating the selected object about an axis that passes through the center of the rotating object.

4. The method of claim 3, wherein the axis is a vertical axis.

5. The method of claim 1, wherein said (a) disposing the objects in the chamber comprises situating the objects all in the same horizontal plane, and said (b) selecting and moving one of the objects to the analysis position comprises moving all of the objects at once in said horizontal plane until said one of the objects arrives at a predetermined position in the chamber.

6. The method of claim 1, wherein said (a) disposing the objects in the chamber comprises placing the objects all in the same horizontal plane, and said (b) selecting and moving one of the objects to the analysis position comprises rotating all of the objects in the horizontal plane about a common vertical axis until said one of the objects arrives at a predetermined position in the chamber.

7. The method of claim 1, wherein said (d) irradiating the rotating object with primary ions comprises producing the primary ions from at least one gas selected from the group consisting of oxygen, cesium, gallium and argon.

8. The method of claim 1, wherein said (d) irradiating the rotating object with primary ions comprises directing the primary ions onto the selected object at an angle of incidence of about 45° to about 90° relative to the selected object.

9. An apparatus for analyzing the composition of an object, comprising:
   a chamber;
   a support disposed in the chamber and configured to support a plurality of objects simultaneously;
   a drive unit operative to rotate each of the objects supported by said plate independently of the other objects at an analysis position in the chamber;
   an ion generator that produces primary ions, and oriented to irradiate with the primary ions an object that is being rotated at said analysis position by said drive unit;
   a detector disposed relative to said ion generator so as to collect secondary ions emitted from the object irradiated by the primary ions; and
   an analyzer connected to said detector so as to receive the secondary ions collected by said detector and operative to analyze the secondary ions.

10. The apparatus of claim 9, and further comprising: a transfer device operatively connected to said support so as to move said support over a range wherein each of the objects supported thereby can be brought to a predetermined position in said chamber.

11. The apparatus of claim 10, wherein said transfer device comprises a rotary driving mechanism that rotates the support about a vertical axis.

12. The apparatus of claim 10, wherein said transfer device comprises a linear driving mechanism that moves the support linearly in a horizontal plane.

13. The apparatus of claim 10, wherein said transfer device comprises a linear motor connected to the support, the linear motor reciprocally moving the supporter.

14. The apparatus of claim 10, wherein said transfer device comprises an X-axis rail extending horizontally in said chamber, a Y-axis rail extending horizontally in said chamber substantially perpendicular to the X-axis rail, and linear motors mounted on said X-axis and Y-axis rails, respectively.

15. The apparatus of claim 9, wherein said support comprises a plate having holes therethrough at locations dedicated for supporting the objects.

16. The apparatus of claim 15, wherein said drive unit is disposed under said plate, and said drive unit comprises an arm, and at least one driving mechanism operatively connected to said arm so as to rotate said arm and move said arm vertically toward and away from said plate.

17. The apparatus of claim 15, wherein said plate is square, and the holes are arrayed in rows and columns across the plate.

18. The apparatus of claim 15, wherein said plate is circular, and the holes are arrayed along the circumference of the plate.

19. The apparatus of claim 9, wherein said ion generator is inclined at an angle of about 45° to about 90° relative to the plane in which an object will lie when the object that is being rotated at said analysis position by said drive unit.

20. The apparatus of claim 9, wherein said ion generator comprises at least one source of gas selected from the group consisting of oxygen, cesium, gallium and argon.

21. The apparatus of claim 9, wherein said detector comprises an electron multiplier, a faraday cup or an ion sensitive image amplifier.

22. The apparatus of claim 9, wherein said analyzer comprises a magnetic mass analyzer, a quadrupole mass analyzer or a time of flight mass analyzer.

* * * * *